(12) United States Patent
Greenslet et al.

(10) Patent No.: US 11,590,625 B2
(45) Date of Patent: Feb. 28, 2023

(54) DEBURRING TECHNIQUE FOR STENTS

(71) Applicant: University of Florida Research Foundation, Incorporated, Gainesville, FL (US)

(72) Inventors: Hitomi Greenslet, Gainesville, FL (US); Mingshuo Li, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 498 days.

(21) Appl. No.: 16/407,673

(22) Filed: May 9, 2019

(65) Prior Publication Data
US 2019/0366501 A1 Dec. 5, 2019

Related U.S. Application Data

(60) Provisional application No. 62/678,599, filed on May 31, 2018.

(51) Int. Cl.
*A61F 2/82* (2013.01)
*B24B 9/02* (2006.01)

(52) U.S. Cl.
CPC .............. *B24B 9/02* (2013.01); *A61F 2/82* (2013.01); *A61F 2240/001* (2013.01)

(58) Field of Classification Search
CPC .................................. B24B 9/00; B24B 9/04
See application file for complete search history.

(56) References Cited

U.S. PATENT DOCUMENTS

| | | | | | |
|---|---|---|---|---|---|
| 3,540,168 | A | * | 11/1970 | Sawert | B24B 9/00 451/36 |
| 3,594,955 | A | * | 7/1971 | Collin | B24B 5/35 451/242 |
| 4,580,370 | A | * | 4/1986 | Smith | B24B 5/22 451/11 |

(Continued)

FOREIGN PATENT DOCUMENTS

WO WO-2017066420 A1 * 4/2017 ........... B24B 31/112

OTHER PUBLICATIONS

Du et al., Surface Finishing of Metallic Biodegradable Stent, [article, online], 2015, <URL: https://www.researchgate.net/publication/317905486_1007_Surface_Finishing_of_Metallic_Biodegradable_Stent> (4 pages).

(Continued)

*Primary Examiner* — Cachet I Proctor
(74) *Attorney, Agent, or Firm* — Alston & Bird LLP

(57) ABSTRACT

An apparatus and method is provided for finishing surfaces and edges of a stent. The apparatus may be capable of rotating a turning wheel, lowering the turning wheel onto a stent, tilting the stent, and polishing and deburring exterior, interior, and wall surfaces of the stent. An automated method is provided for polishing and deburring exterior, interior, and wall surfaces of a stent. Additionally, the automated method may include rotating a turning wheel, applying magnetic abrasive particles to the turning wheel, lowering the turning wheel onto the stent, tilting the stent, and polishing and deburring the exterior, interior, and wall surfaces of the stent.

18 Claims, 8 Drawing Sheets

(56) References Cited

U.S. PATENT DOCUMENTS

| | | | | |
|---|---|---|---|---|
| 4,656,789 | A * | 4/1987 | Schwar | B24B 41/061 |
| | | | | 451/246 |
| 8,708,778 | B2 * | 4/2014 | Greenslet | B24B 1/005 |
| | | | | 451/51 |
| 8,715,038 | B2 * | 5/2014 | Cheon | B24B 27/033 |
| | | | | 451/66 |
| 2003/0216109 | A1 * | 11/2003 | Riviere | B24B 5/38 |
| | | | | 451/36 |
| 2006/0065518 | A1 * | 3/2006 | Aiura | B24B 5/40 |
| | | | | 204/212 |
| 2011/0301691 | A1 * | 12/2011 | Kamikihara | B24B 31/112 |
| | | | | 623/1.15 |
| 2012/0088440 | A1 * | 4/2012 | Greenslet | B24B 1/005 |
| | | | | 451/540 |
| 2015/0017882 | A1 * | 1/2015 | Greenslet | B23Q 17/09 |
| | | | | 451/36 |
| 2015/0093970 | A1 * | 4/2015 | Greenslet | B24B 31/112 |
| | | | | 451/59 |

OTHER PUBLICATIONS

Du, Xueyu. *Surface Finishing of the Biodegradable Stent*, M.S. Thesis, University of Florida, Gainesville, FL, (2015), (78 pages).

Pham, Timothy. *The Surface Finishing of Biodegradable Stents*, M.S. Thesis, University of Florida, Gainesville, FL (2016), (76 pages).

*Developing Hearts—Dr. Martin Bocks Seeks to Solve Big Cardiology Problems in Small Children*, SME—Humans of Manufacturing, [article], [online], (2 pages). [Retrieved from the Internet Mar. 26, 2018] <http://www.sme.org/humans-of-manufacturing.aspx>.

* cited by examiner

DEBURRING TECHNIQUE FOR STENTS

CROSS-REFERENCE TO RELATED APPLICATIONS

This application claim priority to U.S. Provisional Patent Application Ser. No. 62/678,599, filed on May 31, 2018, the contents of which are hereby incorporated by reference in their entirety.

FIELD OF INVENTION

The present disclosure relates to surface and edge finishing of stents, more particularly, the apparatus and automated method for mechanically deburring surfaces of a stent.

BACKGROUND

Coronary artery disease is caused by plaque forming on the inner walls of troubled blood vessels, thus reducing the flow of blood, oxygen, and nutrients through the body. In order for the blood vessels to expand and allow normal flow again, biodegradable metallic stents are placed within the troubled blood vessels. The biodegradable metallic stents are designed to be surgically placed within the blood vessel and then are expanded to hold the inner walls of the blood vessel at a fixed diameter, allowing the blood vessel to heal around the stent thus healing the blood vessel. A coating is placed on the biodegradable metallic stents and the effectiveness of the stents depends upon the surface finishing of the stent, as unevenness such as burrs influence the degree of asperity penetration through a coating placed on the stent.

Manufacturing of a mesh stent starts with metallic alloy ingots produced from raw materials. The metallic alloy ingots are initially prepared through induction melting and solution heat treatment. After being prepared the metallic alloy ingots are cut into cylindrical billets. Through a process of repeated cutting and hot extrusion of the cylindrical billets, thin-walled tubes are formed. The thin-walled tubes go through an annealing process followed by cold drawing. Use of a fixed wire mandrel in the cold drawing process increases the accuracy and consistency of the stents' diameter and thickness. Lastly, the tubes are laser cut to form mesh stents. During the manufacturing process of a stent, unevenness forms on all of the surfaces of the stent. The unevenness is in the form of burrs, pits, and semicircular grooves.

Previous methods of surface finishing involved placing the stent and a conductive metal into an electrolyte bath, and then connecting an electrical source to the conductive metal and the stent. As current passed through the now formed closed circuit, a localized anodic dissolution and oxidation generates on the surface of the stent. The resulting process primarily removes material in areas where there are micro-projections, but additionally removes material in other areas. The final results give a smooth and glossy surface, however; the high weight loss of the stent and a large width reduction of the stent strut reduces the real life of the implanted stent.

SUMMARY

Accordingly, an objective of this present disclosure is to provide an apparatus and automated methods for mechanically finishing surfaces and edges of stents. Deburring methods are provided for exterior and interior surface finishing along with deburring methods for wall-surface finishing.

In accordance with an example embodiment of the present disclosure, an apparatus is provided for deburring the surfaces of a stent that may be configured to rotate a turning wheel and lower said turning wheel onto a stent, which may be mounted on a rod. The apparatus may further be configured to deburr an exterior and interior surface of the stent. The exterior surface of the stent may be deburred by the apparatus by friction produced between the turning wheel and the stent. Interior surface of the stent may be deburred by the apparatus by friction between the stent and the rod.

In accordance with another example embodiment of the present disclosure, an automated method is provided for deburring external and internal surfaces of a stent. The automated method may comprise rotating a turning wheel and lowering said turning wheel onto a stent, which is mounted on a rod. The automated method may further be configured to deburr an exterior surface of the stent due to friction between the turning wheel and the stent. Additionally the automated method may deburr an interior of the stent due to friction between the rod and stent.

In accordance with another example embodiment of the present disclosure, an automated method is provided for deburring exterior, interior, and wall surfaces of a stent. The automated method may comprise of rotating a turning wheel. The turning wheel may comprise a magnet inside. The automated method may further comprise applying magnetic abrasive particles to the turning wheel, and lowering said wheel onto the stent. Additionally, the automated method may comprise deburring the exterior, interior, and wall surfaces of the stent.

In accordance with another example embodiment of the present disclosure, an apparatus for deburring wall surfaces of a stent may be configured to settle bristles, of an automated brush, into holes of the stent. The apparatus may also be configured to rotate an eccentric cam, move an automated brush holder wherein the automated brush is mounted, and deburr the wall surfaces of the stent caused by the reciprocation of the bristles against the wall surfaces of the stent.

In accordance with another example embodiment of the present disclosure, an automated method is provided for deburring wall surfaces of a stent, using an automated brush. The automated method may comprise settling bristles of an automated brush, into holes of the stent. The automated method may further comprise rotating an eccentric cam, moving an automated brush holder wherein the automated brush is mounted, and deburring the wall surfaces of the stent caused by the reciprocation of the bristles against the wall surfaces of the stent.

BRIEF DESCRIPTION OF THE DRAWINGS

Some embodiments of this present disclosure may be further understood by the detailed descriptions and corresponding figures.

DETAILED DESCRIPTION

Figure 1:
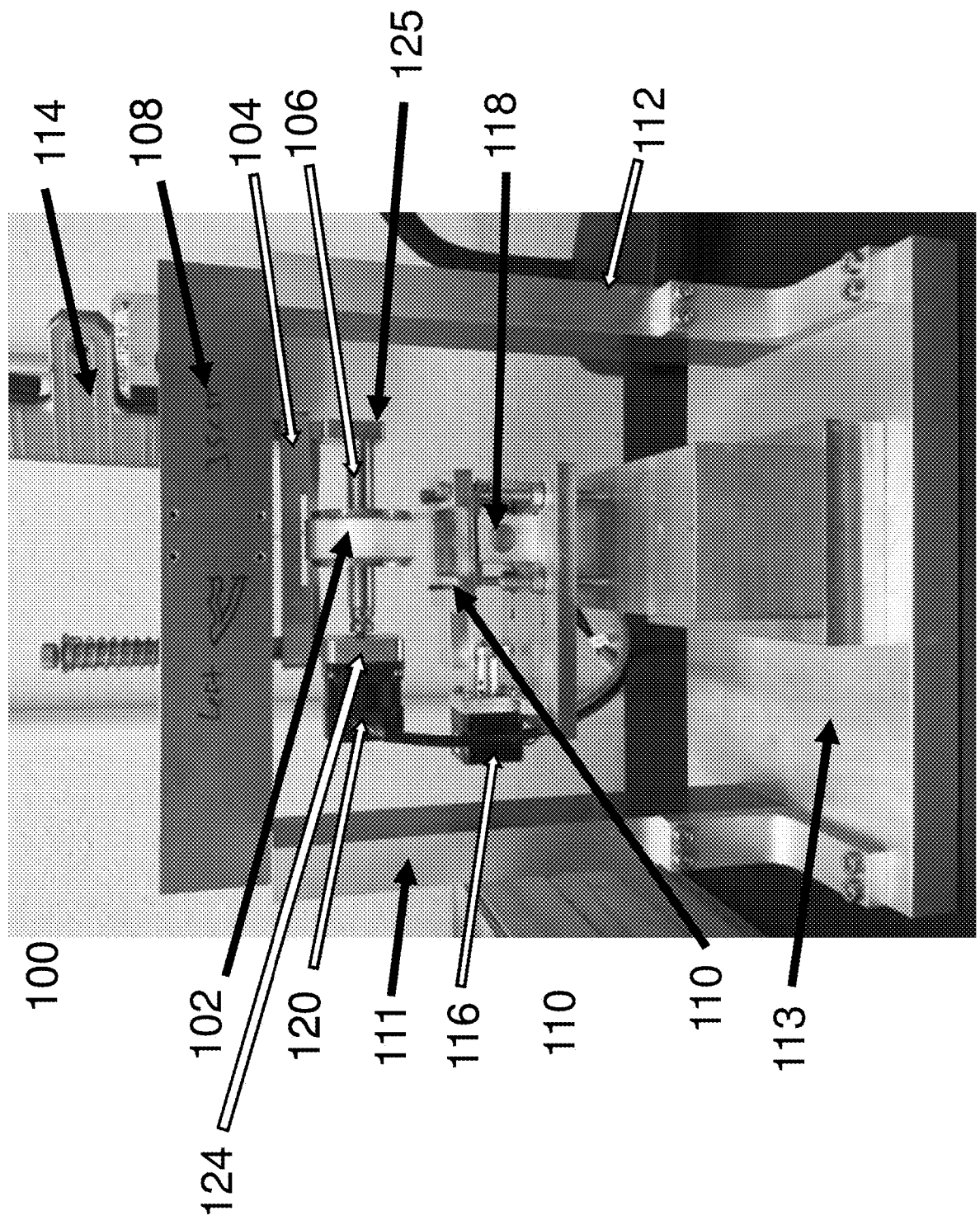
FIG. 1 is a diagram that illustrates the apparatus according to an example embodiment of the present disclosure.

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. Automated methods may be described in a defined order. However, it is understood that any of the automated methods may be performed before or after the other automated methods in the present disclosure. The stents described in the present disclosure in preferred embodiments comprises of a biodegradable magnesium alloy, however; may comprise of any type of metal or biodegradable metal. The use of the term deburr is not intended to limiting the present disclosure to the singular use of removing burrs, but is instead intended to mean removing material to reduce unevenness to result in a smoothed or polished surface in addition to a rounded edge.

Metallic biodegradable stents, particularly those of magnesium alloy, may have a high rate of biodegradation which poses a challenge to their use and reliability. An effective approach to delaying degradation of magnesium alloys is surface modification, such as the use of drug-polymer coatings. More specifically, the corrosion resistance may be enhanced by modifying the metallurgical microstructures and surface chemistry of the relevant alloys. Surface smoothing may enhance corrosion resistance, while also providing a robust surface to receive coatings and to facilitate deliverability of the metallic biodegradable stent.

After the initial operations of manufacturing metallic stents, the surface of the stent is typically uneven and may have burrs, pits, grooves, etc. Rough surfaces on a stent may influence the degree of asperity penetration through the coating applied to the metal substrate before use in a patient. As a result, the high surface roughness becomes a barrier to the real contact between the stent surfaces and the coating surfaces. Therefore, surface finishing becomes an essential factor in manufacturing high quality stents.

Embodiments provided herein include a method to deburr all surfaces of stents. Numerous complexities are involved in deburring stents due to their small size, delicate construction, and their geometrically complex surface. Embodiments described herein provide novel means for fixing the stent during deburring without permanent deformation or fracture, deburring the discontinuous surfaces of the stent, ensuring low material removal while maintaining the biodegradability and mechanical strength of the stent.

Described herein are apparatuses and methods for deburring the stent using mechanical means that result in uniform surface finish with minimal material loss. Such methods include deburring interior, exterior, and wall surfaces of a stent by generating friction on the exterior, interior, and wall surfaces of the stent. The friction is generated by a rotating wheel that applies friction to magnetic abrasive particles and the stent and causes the stent to rotate against the magnetic particles and a rod. A tilting table is tilted during this process to reciprocate the stent against the magnetic abrasive particles and rod, thus further facilitating deburring the surfaces of the stent.

Methods for deburring exterior, interior, and wall surfaces of the stent, described in greater detail below, include the use of magnetic abrasive particles to generate friction against all of the surfaces of the stent, and may include the use of an automated brush to generate said friction against the wall surfaces. When magnetic abrasive particles are used, the magnetic abrasive particles are pressed into and out of the holes of the stent by a magnet and a rotating wheel, in which the magnet lies. The wheel is rotating the stent and thus allowing the stent to be uniformly deburred as all of the surfaces of the stent are pressed against by the magnetic abrasive particles. An automated brush may additionally or substitutably be used to deburr the wall surfaces by the use of bristles to generate a friction against the wall surfaces. An abrasive slurry can be added to this method to increase the friction of the bristles on the wall surfaces. Said automated brush may move and/or vibrate said bristles in a way that provides the correct amount of friction to deburr the wall surfaces of the stent.

It is important that the correct amount of friction is applied in all of the methods by all of the apparatuses, as applying too much or too little friction results in an unusable stent. Use of the apparatuses, and the configuration of said apparatuses, that provide for these automated methods to deburr the stent is additionally described herein.

FIG. 1 is an example diagram of an apparatus 100 configured to deburr all surfaces of a stent. The apparatus may include a first wall 111, second wall 112, base 113, ceiling wall 108, clamp 114, turning wheel 102, bridge 104, shaft 106, tilting table 110, first slide 124, second slide 125, motor 120, and rotatable pivot 118. In an example embodiment, the apparatus may be assembled on an aluminum alloy frame and two aluminum alloy blocks. According to the illustrated embodiment, the frame of the apparatus is defined by a first wall 111 and second wall 112 mounted on the base 113. The frame also is defined by a ceiling wall 108 mounted atop the first wall 111 and extending across the apparatus where it is further supported by the second wall 112.

Specific measurements are used herein for an example embodiment of an apparatus for performing the described techniques; however, the apparatus described herein may be scaled to a wide range of sizes while implementing the same techniques to achieve the common goal of stent deburring.

According to an example embodiment, the thickness of the turning wheel 102 may be about 30 mm, and the diameter may be around 50 mm. A magnet may be set at the center of the turning wheel 102, which may have a thickness of around 6 mm. With the magnet set at the center of the turning wheel 102, the turning wheel 102 may be mounted at the center of the shaft 106. The turning wheel 102 may be placed in the middle of the shaft 106 that is connected to two linear slides, which are mounted inside two bearings. The shaft 106 may be connected from a first slide 124 to a second slide 125. The first slide 124 may be mounted inside a bearing, and the second slide 125 may be mounted inside a second bearing. A motor 120 may be connected to the first slide 124 and adjustably rotates the shaft 106, thus rotating the turning wheel 102.

A bridge 104 is connected to the first slide 124 and connects to the second slide 125. The clamp 114 may hold either the first slide or second slide 125 and may be capable of adjusting the position of the turning wheel 102. The tilting table 110 may be directly below the turning wheel 102 and mounted on a rotatable pivot 118, as depicted in FIG. 1. Two small-diameter springs may support the bottom of two screws which are mounted on the right side of the tilting table to help it stay balanced when the eccentric cam 116 starts rotating. The eccentric cam 116 may be placed under a side of the tilting table 110, and when rotating the eccentric cam 116 may be capable of rising and lowering the side of the tilting table 110. There are two slots on the table. The narrow slot having two screws may be used for fixing a steel rod. The wide slot may provide space for the movement of the stent during the deburring process.

The motor 120 and eccentric cam 116 may be remotely or directly controlled. A microcontroller within the eccentric cam 116 may receive signals from a computer program or manual knob to drive and control the rotational speed of the eccentric cam 116. A manual knob or computer program adjusts the rotating speed of the shaft 106 and the turning wheel 102, by adjusting the speed at which the motor 120 rotates said shaft 106.

Figure 2:
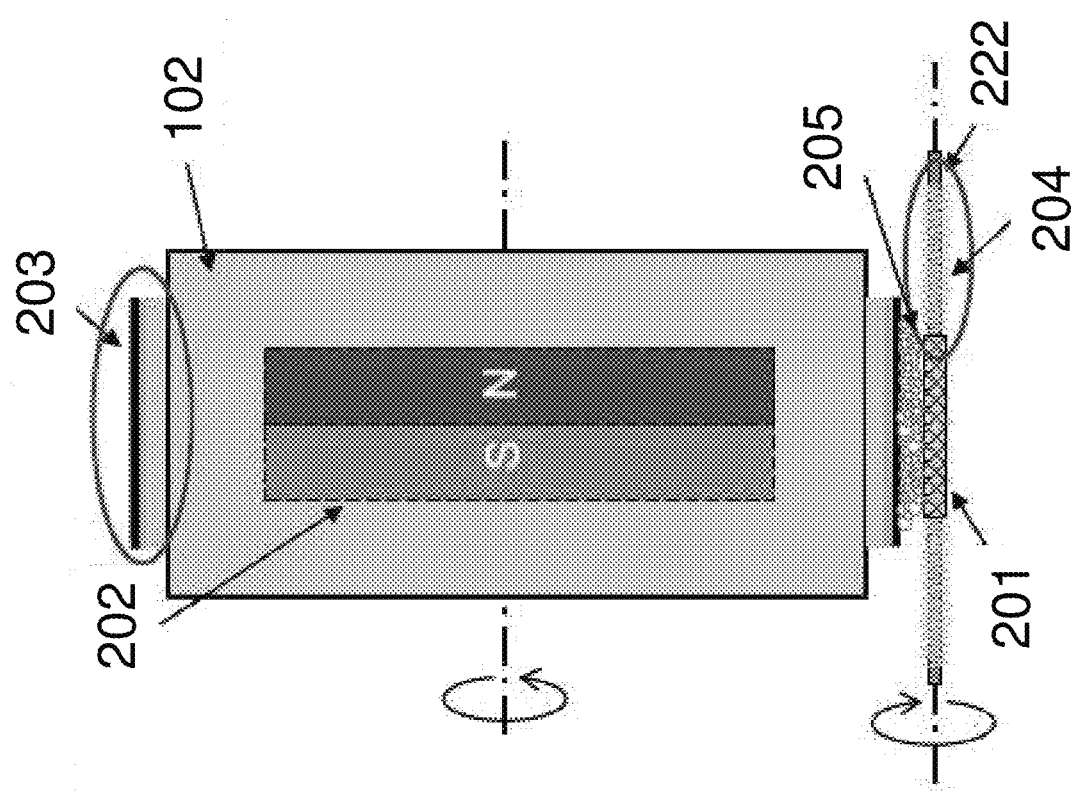
FIG. 2 is a diagram that illustrates the automated method of deburring the exterior and interior surfaces of a stent according to an example embodiment of the present disclosure.
Figure 3:
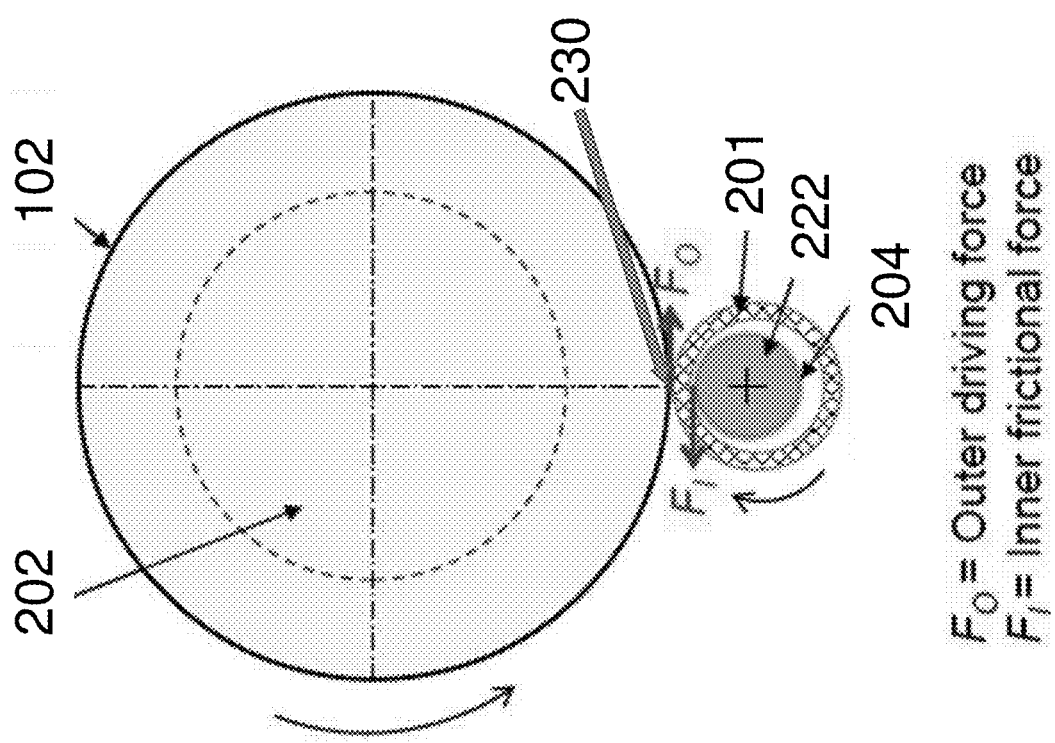
FIG. 3 is a cross-sectional diagram that illustrates the automated method of deburring the exterior and interior surfaces of a stent according to an example embodiment of the present disclosure.

An example embodiment of the automated method of deburring the exterior and interior surfaces of a stent are illustrated in FIG. 2 and FIG. 3. In the example embodiment, the turning wheel 102 may include a magnet 202 set in the center. Tape layers 203 may be wrapped around the turning wheel 102 and may provide additional stability to the turning wheel 102 while the turning wheel 102 is in contact with the stent 201. Additionally the tape layers 203 may provide a frictional force against the stent 201. In this example embodiment, there may be three tape layers comprising a first tape layer of wool tape used to absorb the vibration between the wheel and the stent, a second tape layer of surgical tape used to bridge the gap or smooth the overlap at the connection part of two ends of the wool tape so that the turning wheel can stably contact with the stent without bobbing, and a third layer of gaffer's tape used to increase the friction force between the wheel and the stent.

It is understood that any combination and/or plurality of tape layers may be used. It is also understood that provided benefits of stability and friction from the tape layers 203, may also be combined into the turning wheel 102 itself. That is to mean the turning wheel 102 may be defined by a set of materials such that the tape layers 203 are not needed. In an example embodiment where the tape layers 203 may not be needed, the turning wheel 102 may comprise of material that allow the turning wheel 102 to remain in stable contact with the stent 201, in addition to the outside of the turning wheel 102 comprising of a material for generating a frictional force against the stent 201.

The stent 201 may be mounted on a steel rod 222. The rod 222 in this example embodiment is made of steel, however; the rod 222 may be made of any material capable of being attracted upward by a magnet 202. The steel rod 222 may additionally include a wrapping thread 204 on the outside of the rod 222. The wrapping thread 204 may be used to deburr the interior surface of the stent 201 by adding friction against the interior surface of the stent 201 and may be made of polyester thread. It is understood that the materials of the wrapping thread 204 may include different materials capable of providing the same or similar friction to the interior surface of the stent 201. It is also understood that the steel rod 222 may include materials capable of supplying friction to the interior surface of the stent 201, thus removing the need for the wrapping thread 204.

FIGS. 2 and 3 depict a schematic illustration of the example embodiments of an apparatus and method for stent deburring according to the present disclosure. According to the illustrated schematic, the automated method of deburring an exterior and interior surface of a stent uses a motor, such as motor 102 of FIG. 1, rotating a shaft, such as shaft 106 of FIG. 1, on which a turning wheel 102 is mounted. As shown in FIG. 1, a clamp 114 may adjust the position of the turning wheel 102 relative to an exterior surface of the stent 201. At the point of contact 230 between the turning wheel 102 and the stent 201, the turning wheel 102 exhibits a normal, downward force on the stent's external surface due to the weight of the turning wheel 102 along with a tangential force generated at the point of contact 230. These forces along with friction, produced by the tape layers 203, cause the stent 201 to rotate in an opposite direction than the turning wheel 102. The magnet 202 attracts the steel rod 222 upward, thus causing the upper interior surface of the stent 201 to be pressed upon by the wrapping thread 204. The attraction upward of the steel rod 222 against the stent 201 allows the wrapping thread 204 to impair the rotation of the stent 201. As the stent 201 rotates, as shown in FIG. 3, the wrapping thread 204 causes friction on the interior surface of the stent that functions to deburr the interior surface of the stent 201. The resulting rotational speed difference between the turning wheel 102 and the stent 201 causes friction that deburrs the exterior surface of the stent 201. Thus, the interior and exterior surfaces of the stent 201 are simultaneously deburred during this process.

According to some embodiments, an abrasive slurry 205 may be added during this process to promote deburring of the stent 201 and producing a smoother surface. The abrasive slurry 205 may include an abrasive material and lubricant. In this example embodiment of the present disclosure the abrasive material is diamond powder, however; the abrasive material may be any hard particles that, when rubbed against the stent 201, remove material from the stent 201. The lubricant of this example embodiment is soluble barrel finishing compound, however; the lubricant may be any liquid that allows the abrasive material to flow to every part of the stent 201.

Figure 4:
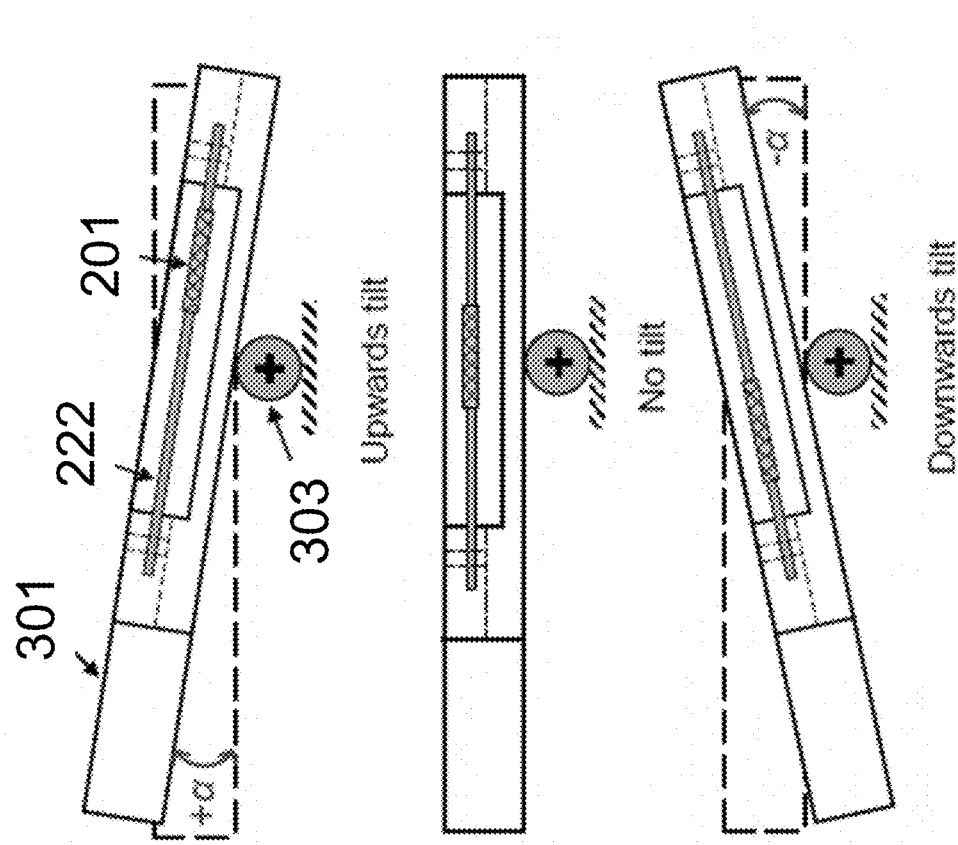
FIG. 4 is a diagram that illustrates the tilting table according to an example embodiment of the present disclosure.

FIG. 4 illustrates a diagram of a tilting table 301 and the motion of the stent 201 along the steel rod 222 during the automated method of deburring the exterior and interior of the stent 201, according to the example embodiments described above. The depicted embodiment of a tilting table 301 is used as the turning wheel 102 rotates the stent 201 and facilitates simultaneous deburring of the interior and exterior surfaces of the stent 201. The steel rod 222 of example embodiments may include a wrapping thread 204 as the tilting table 301 is generally used to further deburr the interior surface of the stent 201 through a change in the angle of interaction between the abrasive surfaces and the stent 201, providing a more complete deburring of the complex surface of the stent.

The stent 201 and the steel rod 222 may be mounted on the tilting table 301, while the tilting table 301 may be mounted on a rotatable pivot 303 that enables the tilting table 301 to be adjustably tilted upward and downward. An eccentric cam may be placed under an end of the turning table 301 and may be driven by a step motor to tilt the tilting table 301 to a tilt angle of +a and −a. As the end of tilting table 301 with the eccentric cam is lifted to a tilt angle of +a, the stent 201 may slide down along the steel rod 222 as depicted in the "Upwards tilt" illustration. As the eccentric cam may lower the same end of the tilting table 301 to a tilt angle of −a, the stent 201 slides down along the steel rod 222 as depicted in the "Downward tilt" illustration.

Sliding of the stent 201 along the steel rod 222, as the turning wheel 102 rotates the stent 201, causes fiction between the stent 201 and the steel rod's wrapping thread 204. The use of the tilting table 301 adds an additional amount of friction that deburrs the interior surface of the stent 201. Adding the tilting table 301 to the process may allow the interior surface and exterior surface of the stent 201 to be simultaneously and equally deburred.

Stent holes are defined by wall surfaces. An automated deburring method for the wall surface finishing is provided herein. The first described method is the automated method of deburring the wall surfaces of a stent using magnetic abrasive particles. This method simultaneously deburr the exterior, interior, and wall surfaces. This method may use a similar apparatus configuration as the automated method to deburr the exterior and interior surfaces. The second automated method for deburring wall surfaces of a stent may use an automated brush, and may use a different apparatus or apparatus configuration to accomplish this deburring.

Figure 5:
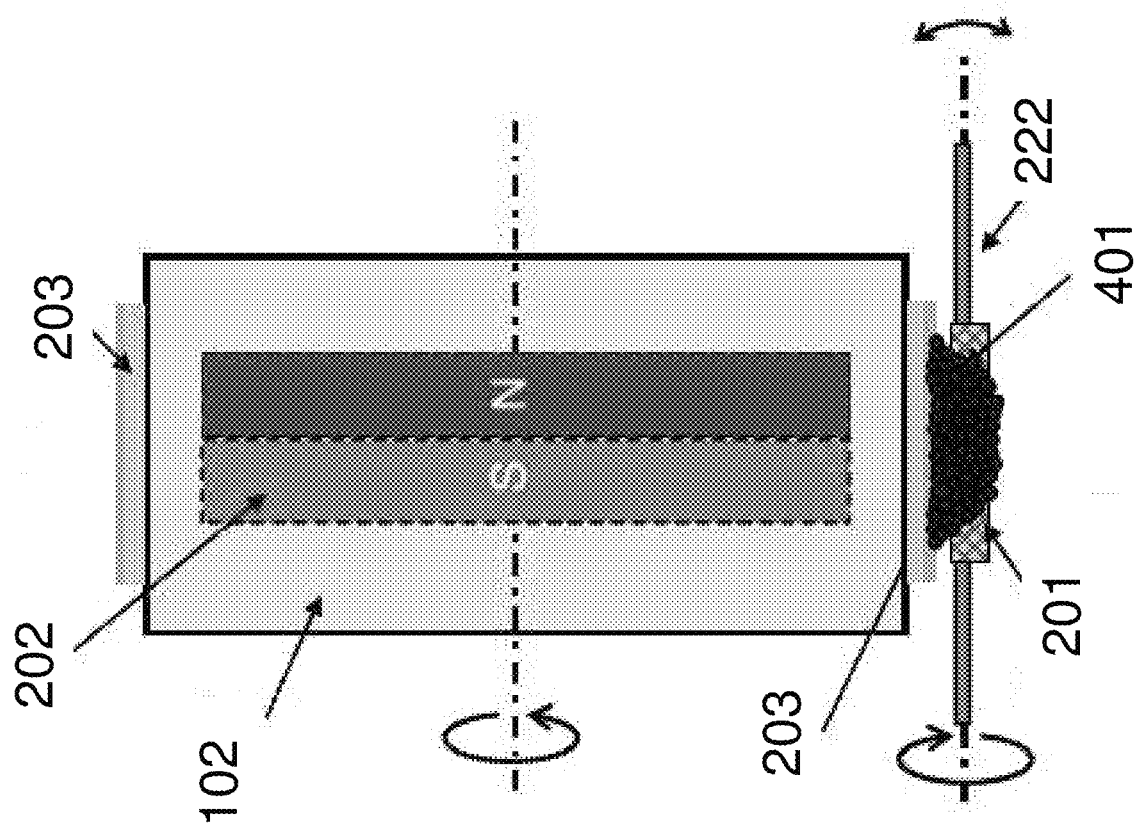
FIG. 5 is a cross-sectional diagram that illustrates the automated method of deburring the exterior, interior, and wall surfaces of a stent according to an example embodiment of the present disclosure.

FIG. 5 illustrates the automated method of deburring of interior, exterior, and wall surfaces of a stent using magnetic abrasive particles. This example embodiment is substantially similar to the previously described automated method of deburring the interior and exterior surfaces of stent 201, sharing many of the same components functioning as described above. According to the illustrated embodiment of FIG. 4, the tape layers 203 and the steel rod 222 may be specifically configured for use with the magnetic abrasive particles. Specifically, the tape layers 203 wrapped around the turning wheel 102 may include two layers. The first layer including wool tape functioning to absorb or dampen the vibration between the turning wheel 102 and the stent 201 while a second tape layer of surgical tape may be used to bridge the gap or smooth the overlap at the connection part of two ends of the wool tape such that the turning wheel 102 can remain in stable contact with the stent 201 without bobbing. The gaffer's tape of the above-described embodiment may optionally be omitted as its function was primarily to increase the friction between the turning wheel 102 and the stent 201, which may no longer be necessary to the basic function of the apparatus.

It is understood that the tape layers 203 may comprise of any combination of a plurality of tape layers. Additionally it is understood that the turning wheel 102 may include the provided benefits of the tape layers 203, thus removing or reducing the need for the tape layers 203.

In this example embodiment, the steel rod 222 may optionally exclude a wrapping thread 204 as the wrapping thread 204 was used to deburr the internal surfaces of the stent 201.

Magnetic or ferrous abrasive particles 401 are added onto the outer surface of the turning wheel 102 along the turning wheel 102 where the stent 201 will contact the turning wheel 102. The magnetic force of the magnet 202 attracts the magnetic particles 401, thus holding the magnetic abrasive particles 401 against the turning wheel 102. The magnetic abrasive particles 401 may comprise of at least one type of magnetic particles and may additionally include abrasive material. The term "magnetic" as used herein references particles that are magnetically attracted to a magnet or exhibiting properties of a magnet themselves. Said magnetic abrasive particles 401 are capable of magnetically attracting to a magnet 202 and are capable of removing material from the wall surfaces of the stent 201 by virtue of their abrasiveness. In the example embodiment, the magnetic abrasive particles 401 may comprise of iron powder, iron powder and diamond powder, or magnetic particles and abrasives (e.g., alumina or silicon carbide). However, it is understood that any plurality of combinations may be used in the magnetic abrasive particles 401 and the sizes of the particles may vary in size.

As the magnetic abrasive particles 401 are attracted to the surface of the turning wheel 102, the turning wheel 102 is rotated. The turning wheel 102 may then be lowered onto the external surface of the stent 201, directly below the turning wheel 102. The stent 201 may be mounted on a steel rod 222 which may be fixed on a tilting table 301, described above. A friction force caused by the magnetic abrasive particles 401 on the turning wheel 102 may cause the stent 201 to rotate in an opposite direction of the turning wheel 401. While the turning wheel 102 rotates the stent 201, the magnetic abrasive particles 401 collect in the holes of the stent 201 thus reciprocating against the exterior, interior, and wall surfaces of the stent 201. Additionally, during this process the tilting table 301 may be tilted at an angle, a, causing the stent 201 to move reciprocally among the magnetic abrasive particles 401.

FIG. 4 illustrates a diagram of a tilting table 301 and the motion of the stent 201 along the steel rod 222 during the automated method of deburring the exterior and interior of the stent 201, according to the example embodiments described above. The depicted embodiment of a tilting table 301, as the turning wheel 102 rotates the stent 201, facilitates simultaneous deburring of the interior and exterior surfaces of the stent 201. The tilting table 301 is generally used to further deburr the interior, exterior, and wall surfaces of the stent 201 through a change in the angle of interaction between the abrasive surfaces and the stent 201, providing more complete deburring of the complex surfaces of the stent.

Figure 6:
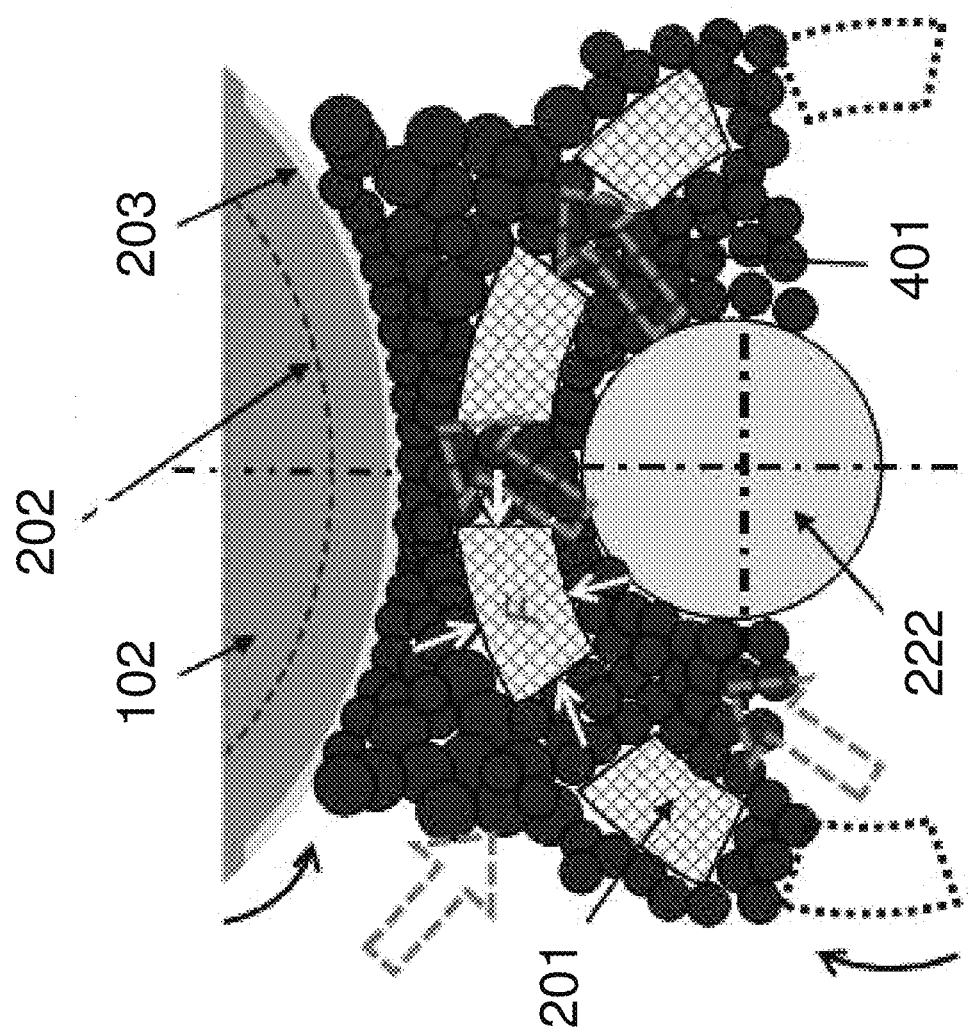
FIG. 6 is a diagram that illustrates a close-up view of the automated method of deburring the exterior, interior, and wall surfaces of a stent according to an example embodiment of the present disclosure.

Two major processes occur during this automated method that allow for the deburring of the wall surfaces of the stent, as depicted in FIG. 6. The first process occurs as the turning wheel 102 rotates against the stent 201. The magnetic abrasive particles 401 are pressed into the stent 201 by the turning wheel 102 and are supported by the steel rod 222. A wall of the stent 201 may be fully surrounded on all sides by the magnetic abrasive particles 401. Thus, the magnetic abrasive particles 401 may be forced towards the wall surfaces of the stent 201 and exert a force onto the wall surfaces. Tilting table 301 may cause the stent 201 to move along the steel rod 222 as the tilting table 301 is tilted. Combining the movement by the stent 201 along the steel rod 222 and the exerted force onto the wall surfaces, the wall surfaces are rubbed against by the magnetic abrasive particles 401 which results in the deburring of the wall surfaces.

The second process occurs when the magnetic abrasive particles 401 are pressed into the holes of the stent 201 and then attracted back out of the holes by the magnet 202. As the magnetic abrasive particles 401 are pressed into the stent 201, the exerted force onto the wall surfaces by the magnetic abrasive particles 401 cause friction against the wall surfaces. Additionally, as the stent 201 and turning wheel 102 rotate opposite of each other, the magnetic abrasive particles 401 are attracted out of the holes by the magnet 202 in the turning wheel 102. This causes friction as the magnetic abrasive material 401 is attracted out of the holes. Thus, the resulting in-and-out movement of the magnetic abrasive particles 401 during this process causes further deburring of the stent 201 exterior, interior, and wall surfaces and the edges of the holes.

Another example of an automated method of deburring the wall surfaces of a stent may involve the use of an automated brush. Due to the small size and irregular shape of the holes in the walls of stents, automated brush bristles may be used to enter through the holes of a stent and deburr the wall surfaces. These bristles may be made of softer material than the stents thus will not excessively deform or crack the stent when pressed and moved along the wall surfaces. Additionally, the bending strength and toughness of the bristles along with the movement of the bristles by the automated brush allow for deburring of the wall surfaces.

Figure 7:
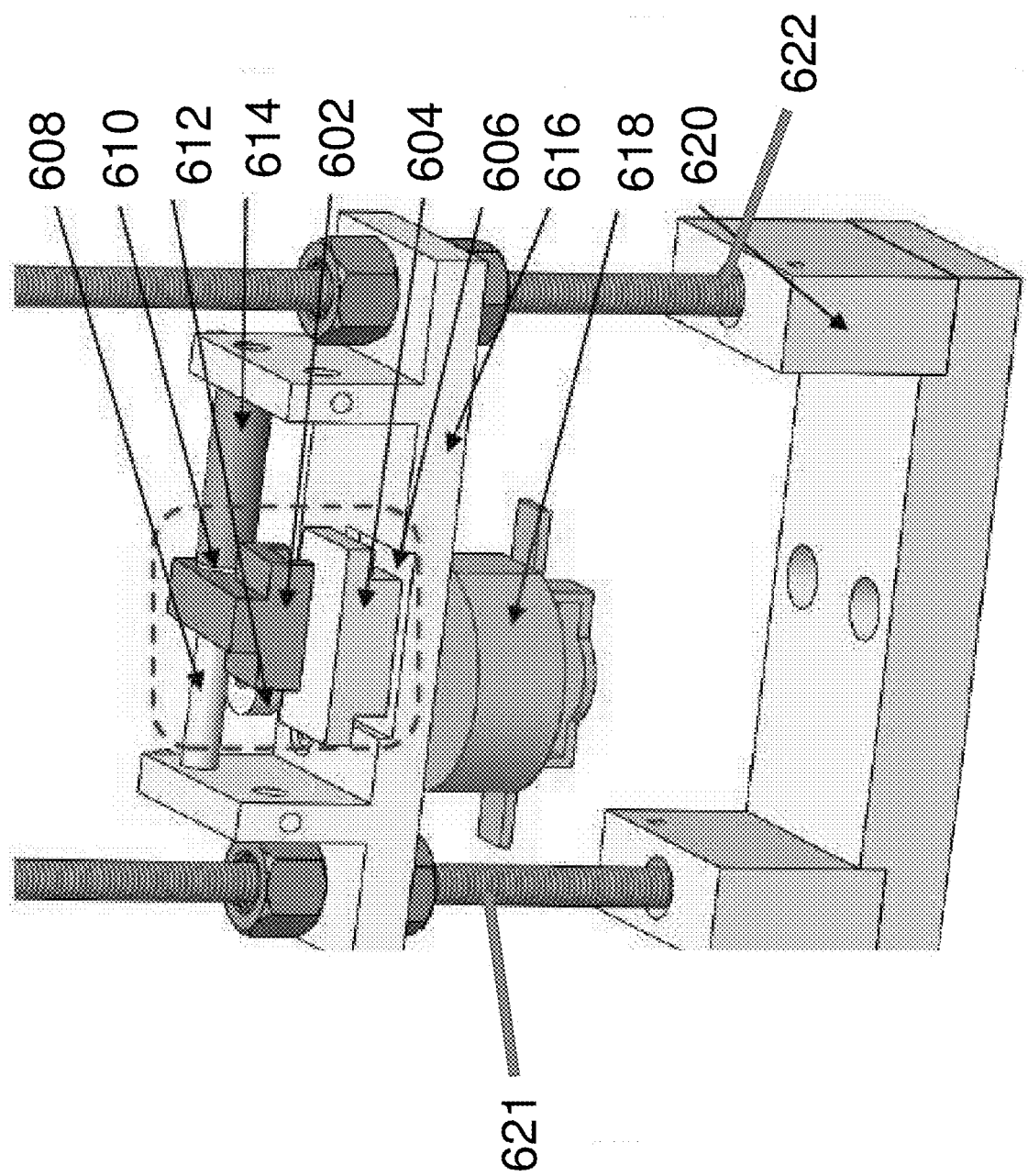
FIG. 7 is a diagram that illustrates an automated method of deburring the wall surfaces of a stent using an automated brush according to an example embodiment of the present disclosure.

FIG. 7 is an example apparatus configured to deburr the wall surfaces of a stent by using an automated brush. The apparatus 600 is defined by a frame and includes an automated brush holder 602, stent stand 604, plane groove 606, shaft 608, bearing 610, eccentric cam 612, spring 614, lifter 616, and motor 618. The frame includes a base 620, first pole 621 and second pole 622. It is appreciated that the components of the illustrated embodiment represent one configuration of the apparatus including various adjustable features that may not be necessary on a commercialized or more mass-produced implementation. As such, features of the illustrated embodiment should be interpreted as one configuration of a possible apparatus while other configurations, potentially with more or fewer features or adjustable elements may also be configured substantially similarly to that which is illustrated and described without deviating from the scope of the disclosure.

According to the illustrated embodiment, the lifter 116 may serve as frame for the rest of the components and one end of the lifter 116 is connected to the first pole 621 and the other end is connected to the second pole 622. The lifter 116 may be positional adjustable along the first pole 621 and second pole 622. The motor 618 may be mounted to the bottom surface of the lifter 116. The eccentric cam 612 may be attached to a rotation shaft of the motor 618 through a hole of the lifter 616. Above the stent stand 604, the automated brush holder 602 may be set in the bearing 610 for smooth movement on the shaft 608, on which the automated brush holder 602 is mounted. Both ends of the shaft 608 may be mounted to walls of the lifter 616. A spring 614 may optionally be mounted on the shaft 608 and set such that it is in contact with the right side of the automated brush holder 602.

The stent stand 604 may be mounted on the plane groove 606 located on the top surface of the lifter 116. Between the automated brush holder 602 and the stent stand 604, a clearance may be provided for positioning of a stent that is mounted on a steel rod. An automated brush may be mounted on a slot of the automated brush holder 602 just above the clearance. The eccentric cam 612 is in contact with the left side of the automated brush holder 602, so that when the motor 618 drives the eccentric cam 612 to rotate, the eccentric cam 612 will drive the automated brush holder 602 moving reciprocally on the shaft 608 at the same time.

Figure 8:
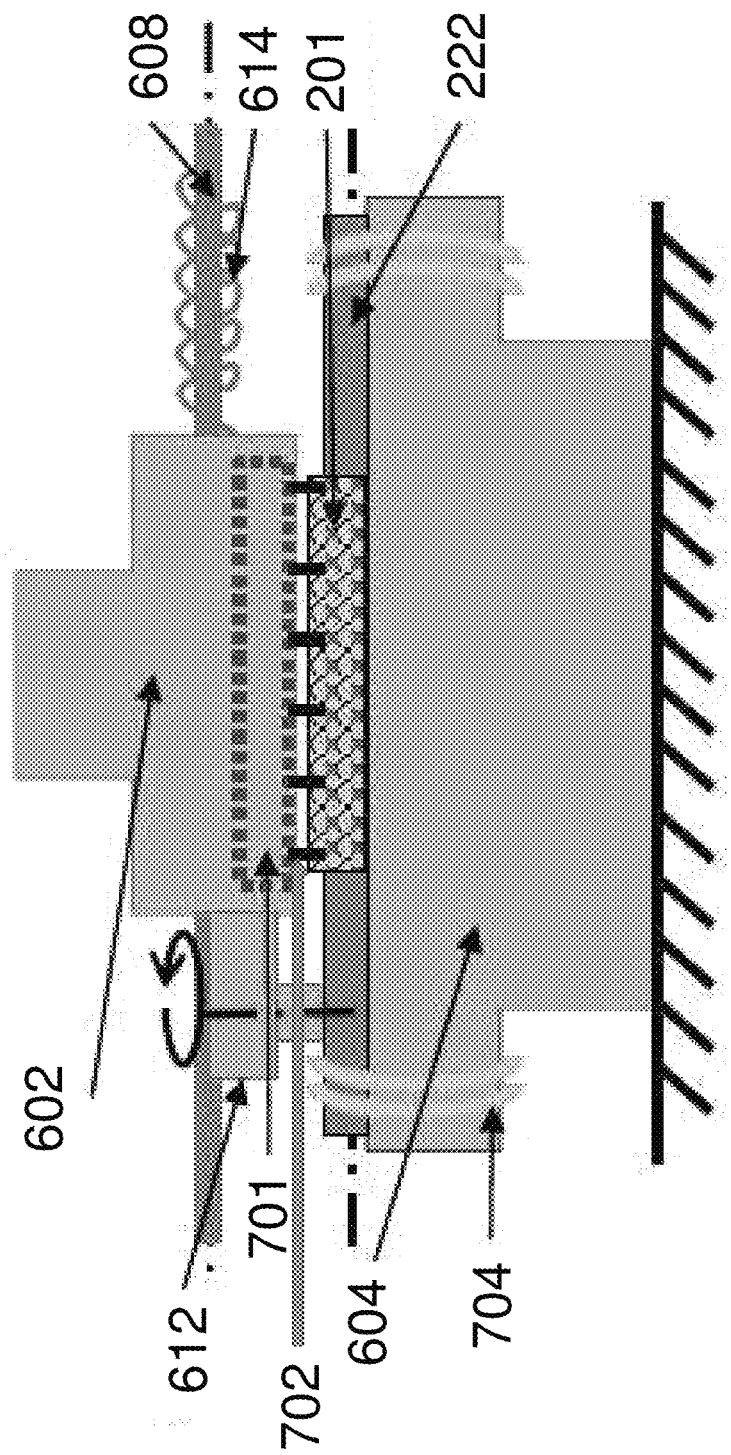
FIG. 8 is a diagram that illustrates a close-up view of the automated method of deburring the wall surfaces of a stent using an automated brush according to an example embodiment of the present disclosure.

FIG. 8 is an illustration of an automated method of deburring the wall surfaces of a stent using an automated brush from the apparatus 600 illustrated in FIG. 6. An automated brush 701 is positioned within the automated brush holder 602, and may include bristles 702. Bristles 702 may be made of polyamide or any other material small enough to fill into the hole of the stent 201 and capable of bending to apply the correct amount of force and friction against the wall surfaces to cause deburring of the wall surfaces. The bristles 702 may also include equal length or different length bristles and/or may have the same or different diameter bristles.

The automated brush 701 may additionally include the ability to hold, angularly vibrate, reciprocally move, and/or linearly vibrate the bristles 702. When the automated brush 701 holds the bristles 702, the automated brush 701 simply holds an end of the bristles 702 and keeping them from falling out. When the automated brush 701 angularly vibrates or reciprocally moves the bristles 702, the automated brush 701 rapidly rotates the bristles back and forth 702. Linearly vibrating the bristles 702 involves the automated brush 701 to oscillate the bristles 702 back-and-forth. The frequency of vibration by the automated brush 701 may be adjustable based on the configuration and needs.

In the clearance left in the apparatus 600, between the automated brush holder 602 and the stent stand 604, a stent 201 which is passed through by a steel rod 222 may be tied on the stent stand 604 by bands 704 to ensure that the stent 201 does move during the deburring process. The steel rod 222 may not include the wrapping thread, as the focus of the deburring operation may be the wall surfaces and not the interior surface. After placing the stent 201 under the automated brush holder 602, multiple bristles 702 of the automated brush 701 may settle into multiple holes of the stent 201. As the eccentric cam 612 is driven by the motor 618, the automated brush holder 602 moves reciprocally on the shaft 608. This movement causes the bristles 702 to deburr the wall surfaces of the stent 201 as they reciprocate against the wall surfaces. The result is simultaneous deburring of wall surfaces of a stent.

An abrasive slurry may be added between the bristles 702 and the stent 201 wall surfaces and pressed by the bristles 702 against the stent 201 wall surfaces. Reciprocating the bristles 702 over the wall surfaces removes the burrs and excess materials from stent 201 wall surfaces. The results of adding an abrasive slurry is that more material from the stent can be removed and the wall surfaces of the stent may be deburred with greater precision.

The above-described mechanical deburring methods for stents may provide improved deburring results of exterior, interior, and wall surfaces of a stent than that of electrolytic polishing.

In some embodiments, certain ones of the operations above may be modified or further amplified. Furthermore, in some embodiments, additional optional operations may be included, some of which have been described above. Modifications, additions, or amplifications to the operations above may be performed in any order and in any combination.

Many modifications and other embodiments of the inventions set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. An automated method for deburring exterior, interior, and wall surfaces of a stent, the automated method comprising:
   rotating a turning wheel;
   applying magnetic abrasive particles to the turning wheel, wherein the turning wheel comprises a magnet;
   bringing the turning wheel toward the stent with clearance between the turning wheel and stent for layers of the magnetic abrasive; and
   deburring the exterior, interior, and wall surfaces of the stent, wherein the wall surfaces are between the exterior surface and the interior surface of the stent, in response to the pressing in of magnetic abrasive particles into holes of the stent by the turning wheel and the pulling out of magnetic abrasive particles from the holes of the stent by the magnet,
   wherein the pressing in of magnetic abrasive particles into holes of the stent by the turning wheel and the pulling out of magnetic abrasive particles from the holes of the stent by the magnet is performed by rotating the turning wheel in a first direction and rotating the stent in a second direction, opposite the first direction.

2. The automated method of claim 1, wherein the stent comprises biodegradable metallic material.

3. The automated method of claim 1, wherein a rod is mounted on a tilting table, and the automated method further comprises:
   tilting the tilting table, wherein the tilting table is mounted on a rotatable pivot;
   allowing the stent to move along the rod, due to the tilting table tilting; and
   deburring the exterior, interior, and wall surfaces of the stent further, due to the friction caused between the stent and magnetic abrasive particles due to the stent movement along the rod.

4. The automated method of claim 1, further comprising a rod onto which the stent is mounted, wherein the exterior, interior, and wall surfaces of the stent are surrounded by the magnetic abrasive particles within the clearance between the turning wheel and the stent and between the rod and the stent.

5. The method of claim 1, further comprising:
   applying an abrasive slurry to the stent, wherein the abrasive slurry comprises the magnetic abrasive particles and a lubricant.

6. The method of claim 1, wherein the rod comprises a wrapping thread configured to increase friction against the magnetic abrasive.

7. A method for deburring the surfaces of a stent comprising:
   rotating a turning wheel, wherein the turning wheel comprises a magnet;
   lowering the turning wheel toward a stent, where the stent is mounted on a rod, with clearance between the turning wheel and the stent for layers of magnetic abrasive; and
   deburring, simultaneously, exterior surfaces, interior surfaces, and wall surfaces of the stent, wherein the wall surfaces are between the exterior surface and the interior surface of the stent, wherein the exterior surfaces are deburred by the friction between the stent and magnetic abrasive pressed by the turning wheel, wherein the interior surfaces are deburred by the friction between the stent and the magnetic abrasive, and wherein the wall surfaces of the stent are deburred by pressing in of magnetic abrasive particles into holes of the stent by the turning wheel and pulling out of the magnetic abrasive particles from the holes of the stent by the magnet of the turning wheel,
   wherein the pressing in of magnetic abrasive particles into holes of the stent by the turning wheel and the pulling out of magnetic abrasive particles from the holes of the stent by the magnet is performed by rotating the turning wheel in a first direction and rotating the stent in a second direction, opposite the first direction.

8. The method of claim 7, wherein the stent comprises biodegradable metallic material.

9. The method of claim 7, wherein the rod is mounted on a tilting table, the method further comprising:
   tilting the tilting table, wherein the tilting table is mounted on a rotatable pivot;
   moving the stent along the rod, in response to the tilt of the tilting table;
   deburring the interior surface of the stent in response to the friction between the stent and magnetic abrasive as the stent moves along the rod; and
   deburring the wall surfaces of the stent in response to the friction between the stent and the magnetic abrasive particles as the stent moves along the rod.

10. The method of claim 7, further comprising:
    applying an abrasive slurry to the stent, wherein the abrasive slurry comprises the magnetic abrasive particles and a lubricant.

11. The method of claim 7, wherein the rod comprises a wrapping thread configured to increase friction against the magnetic abrasive.

12. The automated method of claim 7, further comprising a rod onto which the stent is mounted, wherein the exterior, interior, and wall surfaces of the stent are surrounded by the magnetic abrasive particles within the clearance between the turning wheel and the stent and between the rod and the stent.

13. An automated method for deburring exterior surfaces, interior surfaces, and wall surfaces of a stent, the automated method comprising:
    rotating a turning wheel comprising a magnet;
    lowering the turning wheel toward the stent, wherein the stent is mounted on a rod, with clearance between the turning wheel and the stent for layers of magnetic abrasive;
    deburring the exterior walls of the stent, caused by the friction between the stent and magnetic abrasive pressed by the turning wheel;
    deburring the interior walls of the stent, caused by the friction between the magnetic abrasive and stent; and
    deburring the wall surfaces of the stent, wherein the wall surfaces are between the exterior surface and the interior surface of the stent by pressing of magnetic abrasive particles into holes of the stent by the turning wheel and the pulling out of the magnetic abrasive particles from the holes of the stent by the magnet of the turning wheel while keeping the magnetic abrasive sliding along the exterior, interior, and wall surfaces of the stent,
    wherein the pressing in of magnetic abrasive particles into holes of the stent by the turning wheel and the pulling out of magnetic abrasive particles from the holes of the stent by the magnet is performed by rotating the turning wheel in a first direction and rotating the stent in a second direction, opposite the first direction.

14. The automated method of claim 13, wherein the stent comprises biodegradable metallic material.

15. The automated method of claim 13, wherein the automated method further comprises:
    applying an abrasive slurry to the stent, wherein the abrasive slurry comprises an abrasive material and lubricant.

16. The automated method of claim 13, wherein the rod is mounted on a tilting table, and the automated method further comprises:
    tilting the tilting table, wherein the tilting table is mounted on a rotatable pivot;
    allowing the stent to move along the rod, due to the tilt of the tilting table; and
    deburring the interior surface of the stent further, due to the friction between the stent and magnetic abrasive as the stent slides along the rod.

17. The automated method of claim 13, wherein the rod comprises a wrapping thread configured to increase friction against the magnetic abrasive.

18. The automated method of claim 13, further comprising a rod onto which the stent is mounted, wherein the exterior, interior, and wall surfaces of the stent are surrounded by the magnetic abrasive particles within the clearance between the turning wheel and the stent and between the rod and the stent.

\* \* \* \* \*